United States Patent
Su et al.

(10) Patent No.: US 6,806,364 B2
(45) Date of Patent: Oct. 19, 2004

(54) OPHTHALMIC COMPOSITIONS

(75) Inventors: Shih-Horng Su, Westford, MA (US); George W. Ousler, III, Andover, MA (US)

(73) Assignees: AST Products, Inc., Billerica, MA (US); Ophthalmic Research Associates, Inc., North Andover, MA (US)

(*) Notice: Subject to any disclaimer, the term of this patent is extended or adjusted under 35 U.S.C. 154(b) by 15 days.

(21) Appl. No.: 10/207,376

(22) Filed: Jul. 29, 2002

(65) Prior Publication Data

US 2004/0019130 A1 Jan. 29, 2004

(51) Int. Cl.[7] .................................................. C08L 1/28
(52) U.S. Cl. .......................... 536/43; 514/57; 514/912; 536/44; 524/43; 524/44; 524/417
(58) Field of Search .................... 536/43–44; 524/43–44, 524/417, 436; 514/57, 912; 523/105

(56) References Cited

U.S. PATENT DOCUMENTS

| | | | |
|---|---|---|---|
| 4,039,662 A | 8/1977 | Hecht et al. ................. | 424/180 |
| 5,188,826 A | 2/1993 | Chandrasekaran et al. ....... | 424/78.04 |
| 5,290,572 A | 3/1994 | MacKeen ................... | 424/602 |
| 5,578,578 A * | 11/1996 | Hecht et al. .................. | 514/23 |
| 5,597,559 A | 1/1997 | Olejnik et al. ........... | 424/78.04 |
| 5,770,628 A | 6/1998 | Cantoro ..................... | 514/778 |
| 5,807,585 A | 9/1998 | Martin et al. ............... | 424/613 |
| 5,888,493 A | 3/1999 | Sawaya ................... | 424/78.04 |
| 6,265,444 B1 * | 7/2001 | Bowman et al. ............ | 514/570 |
| 6,297,228 B1 | 10/2001 | Clark ......................... | 514/177 |
| 6,348,508 B1 | 2/2002 | Denick, Jr. et al. ...... | 514/772.4 |

OTHER PUBLICATIONS

Internet, Drugstore.com, "Allergan Refresh Liquigel, Lubricant Eye Drops", 2 pages, Oct. 16, 2002.
Internet, Drugstore.com, "Allergan Refresh Lubricant Eye Drops", 2 pages, Oct. 16, 2002.
Internet, Drugstore, Com, "GenTeal Lubricant Eye Drops", 2 pages, Oct. 16, 2002.

* cited by examiner

Primary Examiner—Peter Szekely
(74) Attorney, Agent, or Firm—Fish & Richardson P.C.

(57) ABSTRACT

An aqueous ophthalmic solution containing 0.2 to 2.5 percent by weight a polymeric demulcent, 0.045 to 0.065 percent by weight a calcium salt, and 0.14 to 1.4 percent by weight a phosphate salt. The solution has a viscosity of 20 to 150 centipoise and is buffered to a pH 5.5 to 8.5.

43 Claims, No Drawings

OPHTHALMIC COMPOSITIONS

BACKGROUND

Dry eye syndrome, one of the most common eye disorders, is usually caused by a reduction of the quantity of tears produced or a decrease in the quality of the tear film that lubricates the eyes. Symptoms include itching, burning, irritation, redness, excessive tearing, blurred vision that improves with blinking, and increased discomfort after reading or watching TV.

There is a correlation between aging and decreased production of eye oil (60% less at age 65 than at age 18). The oil deficiency affects the tear film. Without adequate oil to seal the watery layer, the tear film evaporates faster, leaving dry areas on the cornea. Hot, dry or windy climates, high altitudes, air conditioning, and cigarette smoke also cause dry eye.

A number of approaches exist for treating dry eye. For example, one can supplement the tear film with artificial tears. However, too many applications are often required over the course of the day.

SUMMARY

An aspect of this invention relates to an aqueous ophthalmic solution containing 0.2 to 2.5 (e.g., 0.5 to 0.8) percent by weight a polymeric demulcent, 0.045 to 0.065 (e.g., 0.05 to 0.06) percent by weight a calcium salt, and 0.14 to 1.4 (e.g., 0.3 to 1.2) percent by weight a phosphate salt. The ophthalmic solution has a viscosity of 20 to 150 (e.g., 50 to 90) centipoise and is buffered to a pH 5.5 to 8.5 (e.g., 6 to 8) with a phosphate salt or other suitable salts. It may further contain one or more of the following ingredients: 0.5 to 1.0 percent by weight glycerol, 0.5 to 1.0 percent by weight propyleneglycerol, 005 to 0.05 percent by weight glycine, 0.006 to 0.08 percent by weight sodium borate, 0.025 to 0.10 percent by weight magnesium chloride, and 0.001 to 0.01 percent by weight zinc chloride.

An effective amount of the above-described ophthalmic solution can be used to treat dry eye syndrome, and can also be used to treat another eye disorder if it contains a drug for that disorder. "An effective amount" is the amount which is required to confer remedial or therapeutic effect.

Another aspect of this invention relates to a method of preparing polymeric demulcent-containing ophthalmic compositions, including those described above and others. The method includes immersing a polymeric demulcent in water or in an aqueous solution containing one or more ingredients (e.g., calcium chloride), agitating the water or the aqueous solution at 25° C., i.e., room temperature, to 45° C. (e.g., 30° C. to 45° C.) until the polymeric demulcent is dissolved to form a polymeric demulcent-containing solution, and optionally adding one or more other ingredients to the polymeric demulcent-containing solution.

The ophthalmic solution of this invention, when applied to the ocular surface of a subject, unexpectedly stays longer with the eye and, more importantly prolongs the integrity of the tear film. The extraordinary efficacy of this solution is attributed to its unique composition and the unique method by which it is prepared.

Other features and advantages of the invention will be apparent from the following detailed description, and from the claims.

DETAILED DESCRIPTION

The aqueous ophthalmic solution of this invention has a pH of 5.5 to 8.5 (e.g., 6.0 to 7.4) and a viscosity of 20 to 150 centipoise (e.g., 40–70 centipoise). It can be directly applied onto the ocular surface of a patient.

The aqueous ophthalmic solution contains a calcium salt (i.e., one or more calcium salts, such as calcium chloride and calcium phosphate), a phosphate salt (i.e., one or more phosphate salts, such as sodium phosphate and potassium phosphate), and a polymeric demulcent (i.e., one or more polymeric demulcents, such as polyvinyl alcohol, chitosan, and hydroxypropyl methylcellulose).

The polymeric demulcent, because of its high molecular weight, greatly contributes to the viscosity of the ophthalmic solution regardless of its degree of hydrophilicity or hydrophobicity. It is also capable of forming a matrix to reduce water evaporation after the ophthalmic solution is placed on an ocular surface. Examples of suitable polymeric demulcents, including both homopolymers and copolymers, are: cellulosic polymers (e.g., hydroxypropyl methylcellulose, hydroxypropyl cellulose, hydroxybutyl methylcellulose, hydroxyethyl ethylcellulose, carboxymethyl hydroxyethylcellulose, methylcellulose, carboxymethylcellulose); polyols (e.g., polyethylene glycol 300, polyethylene glycol 400, and polysorbate 80); polysaccharides (e.g., gelatin, sodium hyaluronate, sodium alginate, chitosan, and dextran 70); poly(ethylene oxide); polyvinyl alcohol; povidone; and polyvinyl pyrrolidone.

Optionally, the ophthalmic solution contains glycerol or propyleneglycerol. It may further contain glycine, magnesium chloride, and zinc chloride, all of which are found in natural tears. Sodium borate, a mild antiseptic, and other desirable ingredients may also be included. For obvious reasons, all of the ingredients contained in the solution of this invention must be ophthalmically compatible.

To prepare the ophthalmic solution of this invention, a polymeric demulcent is first dissolved in water or in an aqueous solution that contains one or more of the other ingredients (e.g., a phosphate salt), with the aid of an agitator and at room temperature or a slightly elevated temperature, i.e., 45° C. or lower. More ingredients, if any, can then be added to the polymeric demulcent-containing solution. Also within the scope of this invention is dissolving the polymeric demulcent with some or all of the other ingredients at the same time. Of course, the polymeric demulcent can be conveniently dissolved in a solution that is buffered with a phosphate salt (e.g., a phosphate buffered saline) and contains all the other ingredients. For example, in a phosphate buffered saline, pH 7.2, calcium chloride, as well as other ingredients, is dissolved. Any pH change is adjusted with drops of a concentrated NaOH or HCl solution. Hydroxypropyl methylcellulose is then dissolved in the resultant solution in the manner described above. With each ingredient in a predetermined amount, an ophthalmic solution that contains 0.058 percent by weight calcium chloride, 0.6 to 0.8 percent by weight sodium and potassium phosphates, and 0.6 percent by weight hydroxypropyl methylcellulose can thus be obtained.

The same method can also be used to prepare other polymeric demulcent-containing ophthalmic solutions not within the scope of this invention.

Without further elaboration, it is believed that one skilled in the art can, based on the description herein, utilize the present invention to its fullest extent. The following example, which demonstrates how to prepare and test an ophthalmic solution of this invention, is therefore to be construed as merely illustrative and not limitative of the remainder of the disclosure in any way.

EXAMPLE

To 1000 ml of pyrogen-free water, the chemicals were added in the following order: sodium chloride (9 g), sodium phosphate (dibasic, 3.55 g), potassium phosphate (monobasic, 3.40 g), calcium chloride (0.583 g), magnesium chloride (0.476 g), zinc chloride (0.0154 g), glycerol (10 g), sodium chloride, sodium phosphate and potassium phosphates are the components of phosphate buffered saline. The solution was stirred at ambient temperature for 30 minutes, followed by pH adjustment with pyrogen-free NaOH (1 N) to 7.4 and filtration with a membrane (pore size 0.2 µm) to remove impurities.

0.6 g of hydroxypropyl methylcellulose was added to the filtered solution. The mixture was agitated (100 rpm) at 37° C. until it became clear. The viscosity was measured and, if necessary, adjusted with the filtered solution.

The ophthalmic solution thus obtained was sterilized by filtration. When applied to the eye, it was found to stay for a much longer time than a solution of the same composition prepared by dissolving hydroxypropyl methylcellulose at 80° C. The solution was also subjected to a "tear film break-up time" or "TFBUT" test. TFBUT, an index of the severity of dry eye syndrome, can be used to measure the efficacy of a solution in maintaining the tear film.

In this TFBUT test, a patient's eye was first instilled with 5 microliters of 2% sodium fluorescein. After the fluorescein instillation, the patient placed his or her head in a slit lamp, and the investigator viewed the eye under cobalt blue illumination. The patient was instructed to blink three times and hold the eyes open at normal aperture after the third blink.

A stop watch was started when the eye was opened on the third blink, and was stopped when the investigator identified a region of tear film break-up that had started to expand. This region of tear film break-up was identifiable by black voids in the otherwise green fluorescing tear film. The eye was video taped during the test.

The efficacy of the ophthalmic solution prepared above on the TFBUT in seven dry-eye patients was tested as follows: First, a TFBUT baseline for each patient was first established. One or two drops of the ophthalmic solution were then applied into one eye of each patient and the TFBUT was measured at 5, 10, 15, 30, 45, and 60 minutes after the application. The results show that the solution was much more efficacious in prolonging dry-eye patients' TFBUT than three commercial products.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed:

1. An aqueous ophthalmic solution, the solution comprising:

0.2 to 2.5 percent by weight a polymeric demulcent,
   0.5 to 1.0 percent by weight glycerol,
   0.045 to 0.065 percent by weight a calcium salt, and
   0.14 to 1.4 percent by weight a phosphate salt, wherein the solution has a viscosity of 20 to 150 centipoise and is buffered to a pH of 5.5 to 8.5.

2. The solution of claim 1, wherein the solution is buffered with a phosphate salt.

3. The solution of claim 2, wherein the concentration of the calcium salt is 0.05 to 0.06 percent by weight.

4. The solution of claim 3, wherein the concentration of the polymeric demulcent is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

5. The solution of claim 2, wherein the concentration of the calcium salt is 0.058 percent by weight.

6. The solution of claim 5, wherein the concentration of the polymeric demulcent is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

7. The solution of claim 6, wherein the glycerol is 1.0 percent by weight.

8. The solution of claim 2, wherein the glycerol is 1.0 percent by weight.

9. The solution of claim 8, wherein the concentration of the calcium salt is 0.05 to 0.06 percent by weight.

10. The solution of claim 9, wherein the concentration of the polymeric demulcent is 0.5 to 0.8, the concentration of the phosphate salt is 0.3 to 1.2 percent by weight, and the solution has a viscosity of 50 to 90 centipoise and is buffered to a pH of 6.0 to 8.0.

11. The solution of claim 2, wherein the polymeric demulcent is a cellulosic polymer.

12. The solution of claim 11, wherein the concentration of the calcium salt is 0.05 to 0.06 percent by weight.

13. The solution of claim 12, wherein the concentration of the cellulosic polymer is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

14. The solution of claim 11, wherein the cellulosic polymer is hydroxy propylmethylcellulose.

15. The solution of claim 14, wherein the concentration of the calcium salt is 0.05 to 0.06 percent weight.

16. The solution of claim 15, wherein the concentration of the hydroxy propylmethylcellulose is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

17. The solution of claim 2, wherein the calcium salt is calcium chloride.

18. The solution of claim 17, wherein the concentration of the calcium chloride is 0.05 to 0.06 percent by weight.

19. The solution of claim 18, wherein the concentration of the polymeric demulcent is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

20. The solution of claim 17, wherein the concentration of calcium chloride is 0.058 percent by weight.

21. The solution of claim 20, wherein the concentration of the polymeric demulcent is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

22. The solution of claim 17, wherein the cellulosic polymer is a cellulosic polymer.

23. The solution of claim 22, wherein glycerol is 1.0 percent by weight.

24. The solution of claim 23, wherein the concentration of the calcium chloride is 0.05 to 0.06 percent by weight.

25. The solution of claim 24, wherein the concentration of the cellulosic polymer is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

26. The solution of claim 23, wherein the cellulosic polymer is hydroxypropyl methylcellulose.

27. The solution of claim 26, wherein the concentration of the calcium chloride is 0.058 percent by weight.

28. The solution of claim 27, wherein the concentration of the hydroxypropyl methylcellulose is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

29. The solution of claim 28, wherein the concentration of the hydroxypropyl methylcellulose is 0.6 percent by weight, the concentration of the phosphate salt is 0.6 to 0.8 percent by weight, and the solution has a viscosity of 70 centipoise and is buffered to a pH of 6.0 to 7.4.

30. The solution of claim 29, further comprising:

0.005 to 0.05 percent by weight glycine, 0.006 to 0.08 percent by weight sodium borate, 0.025 to 0.10 percent by weight magnesium chloride, and 0.001 to 0.01 percent by weight zinc chloride.

31. The solution of claim 1, wherein the polymeric demulcent is a cellulosic polymer.

32. The solution of claim 31, wherein the concentration of the calcium salt is 0.05 to 0.06 percent by weight.

33. The solution of claim 32, wherein the concentration of the cellulosic polymer is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

34. The solution of claim 33, wherein the glycerol is glycerol is 1.0 percent by weight.

35. The solution of claim 31, wherein the cellulosic polymer is hydroxypropyl methylcellulose.

36. The solution of claim 35, wherein the concentration of the calcium salt is 0.05 to 0.06 percent weight.

37. The solution of claim 36, wherein the concentration of the hydroxypropyl methylcellulose is 0.5 to 0.8 percent by weight, the concentration of the phosphate salt is 0.3 to 1.2 percent by weight, and the solution has a viscosity of 50 to 90 centipoise and is buffered to a pH of 6.0 to 8.0.

38. The solution of claim 37, wherein the glycerol is 1.0 percent by weight.

39. A method for treating an eye, comprising administering to an eye in need thereof an effective amount of the solution of claim 1.

40. A method for treating an eye, comprising administering to an eye in need thereof an effective amount of the solution of claim 31.

41. A method for treating an eye, comprising administering to an eye in need thereof an effective amount of the solution of claim 34.

42. A method for treating an eye, comprising administering to an eye in need thereof an effective amount of the solution of claim 35.

43. A method for treating an eye, comprising administering to an eye in need thereof an effective amount of the solution of claim 38.

* * * * *